(12) United States Patent
Monty et al.

(10) Patent No.: US 7,237,429 B2
(45) Date of Patent: Jul. 3, 2007

(54) CONTINUOUS-RANGE HYDROGEN SENSORS

(75) Inventors: Greg Monty, Vernon Hills, IL (US); Kwok Ng, San Jose, CA (US); Mohshi Yang, Austin, TX (US); Richard Finh, Austin, TX (US)

(73) Assignee: Nano-Proprietary, Inc., Austin, TX (US)

( * ) Notice: Subject to any disclaimer, the term of this patent is extended or adjusted under 35 U.S.C. 154(b) by 58 days.

(21) Appl. No.: 11/063,119

(22) Filed: Feb. 22, 2005

(65) Prior Publication Data

US 2005/0155858 A1    Jul. 21, 2005

Related U.S. Application Data

(60) Continuation-in-part of application No. 10/909,787, filed on Jul. 30, 2004, now Pat. No. 7,104,111, and a continuation-in-part of application No. 10/854,420, filed on May 26, 2004, said application No. 10/909,797 is a division of application No. 10/651,220, filed on Aug. 28, 2003, now Pat. No. 6,849,911.

(60) Provisional application No. 60/475,558, filed on Jun. 3, 2003, provisional application No. 60/407,141, filed on Aug. 30, 2002.

(51) Int. Cl.
*G01N 7/00* (2006.01)

(52) U.S. Cl. .......................................... 73/23.2; 438/48
(58) Field of Classification Search ................. 73/23.2; 438/48; 29/592, 825
See application file for complete search history.

(56) References Cited

U.S. PATENT DOCUMENTS

| 4,240,879 A | 12/1980 | Dobson |
| 5,670,115 A | 9/1997 | Cheng et al. |
| 5,886,614 A | 3/1999 | Cheng et al. |

(Continued)

OTHER PUBLICATIONS

E.C. Walter et al., "Sensors from Electrodeposited Metal Nanowires," *Surface and Interface Analysis*, 2002; 34: 409-412.
Frederic Favier et al., "Hydrogen Sensors and Switches from Electrodeposited Palladium Mesowire Arrays," *Science*, vol. 293, Sep. 21, 2001, pp. 2227-2234.

(Continued)

*Primary Examiner*—Hezron Williams
*Assistant Examiner*—Rodney Frank
(74) *Attorney, Agent, or Firm*—Fish & Richardson P.C.; Kelly Kordzik

(57) ABSTRACT

The present invention provides for novel hydrogen sensors and methods for making same. In some embodiments, such novel hydrogen sensors are continuous-range hydrogen sensors comprising Pd—Ag nanoparticles arrayed as nanowires or two-dimensional shapes on a resistive surface. Such continuous-range hydrogen sensors are capable of measuring a wide range of hydrogen gas concentration over a wide temperature range. Unlike existing hydrogen sensors that experience a large change in resistance at a certain hydrogen concentration, the continuous-range hydrogen sensor of the present invention changes resistance continuously over a broad range of hydrogen concentration. This continuous change varies slowly with hydrogen concentration and is predictable such that the continuous-range hydrogen sensor can be used to measure hydrogen concentration continuously from a few ppm to 40,000 ppm level or higher over a broad range of temperatures (e.g., −40° C. to +150° C.).

20 Claims, 17 Drawing Sheets

U.S. PATENT DOCUMENTS

| | | | |
|---|---|---|---|
| 6,103,540 A * | 8/2000 | Russell et al. | 438/22 |
| 6,120,835 A | 9/2000 | Perdieu | |
| 6,359,288 B1 | 3/2002 | Ying et al. | |
| 6,465,132 B1 | 10/2002 | Jin | 429/231.8 |
| 6,525,461 B1 | 2/2003 | Iwasaki et al. | |
| 6,535,658 B1 | 3/2003 | Mendoza et al. | |
| 6,673,644 B2 | 1/2004 | Gole et al. | 438/49 |
| 6,737,286 B2 * | 5/2004 | Tao et al. | 438/17 |
| 6,770,353 B1 | 8/2004 | Mardilovich et al. | |
| 6,788,453 B2 * | 9/2004 | Banin et al. | 359/342 |
| 6,849,911 B2 | 2/2005 | Monty et al. | |
| 6,882,051 B2 * | 4/2005 | Majumdar et al. | 257/46 |
| 7,104,111 B2 * | 9/2006 | Monty et al. | 73/23.2 |
| 2002/0079999 A1 | 6/2002 | Abdel-Tawab et al. | |
| 2002/0132361 A1 | 9/2002 | Vossmeyer et al. | 436/151 |
| 2003/0079999 A1 | 5/2003 | Penner et al. | 205/775 |
| 2003/0135971 A1 | 7/2003 | Liberman et al. | 29/419.1 |
| 2003/0139003 A1 | 7/2003 | Gole et al. | 438/200 |
| 2003/0189202 A1 * | 10/2003 | Li et al. | 257/14 |
| 2004/0023428 A1 | 2/2004 | Gole et al. | 438/48 |
| 2004/0067646 A1 * | 4/2004 | Tao et al. | 438/689 |
| 2004/0070006 A1 | 4/2004 | Monty et al. | 257/200 |
| 2004/0072213 A1 | 4/2004 | Besnard et al. | |
| 2004/0104129 A1 | 6/2004 | Gu et al. | |
| 2004/0106203 A1 | 6/2004 | Stasiak et al. | |
| 2004/0118698 A1 | 6/2004 | Lu et al. | |
| 2005/0005675 A1 * | 1/2005 | Monty et al. | 73/23.2 |

OTHER PUBLICATIONS

H.D. Tong et al., "A Hydrogen Separation Module Based on Wafer-Scale Micromachined Palladium-Silver Alloy Membranes," *IEEE*, Transducers '03 The 12th International Conference on Solid State Sensors, Actuators and Microsystems, Boston, Jun. 8-12, 2003, pp. 1742-1745.

Minhee Yun et al., "Nanowire Growth for Sensor Arrays," to appear in *Nanofabrication Technologies*, Ed. E. A. Dobisz, SPIE Proceedings 5220, 2003, pp. 1-9.

J. N. Keuler et al., "Characterization of Electroless Plated Palladium-Silver Alloy Membranes," *Thin Solid Films*, 1999, pp. 91-98.

V. Jayaraman et al., "Synthesis and Hydrogen Permeation Properties of Ultrathin Palladium-Silver Alloy Membranes," *Journal of Membrane Science*, 1995, pp. 251-262.

F.A. Lewis, "A Comparison of the Properties of Palladium with Those of Other Transition Elements," The University of Texas Library, Academic Press 1967, pp. 1-31, 48, 50, -51, 56-57, 70-71, 74-79, 82-83,86-87, 90-93, 112-113, 140-141, 144-142, and 160.

Suleiman et al., "The effect of the cluster structure in the phase transition during hydrogen absorption", Annual Reports of Deutsches Elektronen-Synchroton (DESY) (2002).

Suleiman et al., "Pd-H Clusters: non-bulk like behavior", Annual Reports of Deutsches Elektronen-Synchroton (DESY) (2003).

Oh et al., "H NMR Study of Hydrogen in Palladium Nanocrystals", J. Korean Phys. Soc., 43(6) (Dec. 2003), pp. L958-962.

\* cited by examiner

A

B

CONTINUOUS-RANGE HYDROGEN SENSORS

CROSS REFERENCE TO RELATED APPLICATIONS

The present application is a continuation-in-part of the following U.S. patent applications Ser. No. 10/854,420, filed May 26, 2004; and Ser. No. 10/909,797, filed Jul. 30, 2004.

TECHNICAL FIELD

The present invention relates generally to hydrogen sensors, and specifically to continuous range hydrogen gas sensors comprising nanowires and/or arrays of nanoparticles.

BACKGROUND INFORMATION

Hydrogen gas ($H_2$) is widely used in industrial and laboratory settings. Because of its high-flamability in air, the need to detect hydrogen gas at levels below its lower explosive limit (LEL is 4% at 25° C.) is of considerable importance. The use of palladium (Pd) as a hydrogen sensor is well-established (F. A. Lewis, "The Palladium Hydrogen System," Academic Press, New York, 1967) and based on the increased resistance realized when hydrogen dissolves into the metal creating a palladium hydride which has a lower degree of conductivity than pure palladium.

Recently, a palladium nanowire (also known as a "mesowire," where mesoscopic structures are characterized by a length scale ranging from the tens of nanometers to micrometers) sensor has been described which operates with an inverse response, i.e., it realizes a decreased resistance when exposed to hydrogen (United States Patent Application Publication No. US 2003/0079999; United States Patent Application Publication No. US 2004/0238367; F. Favier et al., "Hydrogen Sensors and Switches from Electrodeposited Palladium Mesowire Arrays," Science, vol. 293, pp. 2227–2231, 2001; E. C. Walter et al., "Palladium Mesowire Arrays for Fast Hydrogen Sensors and Hydrogen-Actuated Switches," Anal. Chem., vol. 74, pp. 1546–1553, 2002; G. Kaltenpoth et al., "Multimode Detection of Hydrogen Gas Using Palladium-Covered Silicon µ-Channels," Anal. Chem., vol. 75, pp. 4756–4765, 2003). Such nanowires are electrodeposited, from solutions of palladium chloride ($PdCl_2$) and perchloric acid ($HClO_4$), onto an electrically-biased graphite step ledge (presumably, these terraced step ledges produce an enhanced field leading to selective deposition). Once formed, these nanowires are transferred to an insulating glass substrate using a cyanoacrylate film. The diameters of these wires are reportedly as small as 55 nanometers (nm) and they possess gaps or break-junctions which impart them with high resistance. When hydrogen is introduced, a palladium-hydride ($PdH_x$) forms. At room temperature (25° C.), there is a crystalline phase change from $\alpha$ to $\beta$ when the concentration of hydrogen in air reaches 2% (15.2 Torr). Associated with this phase change is a corresponding 3–5% increase in the lattice parameter of the metal which leads to a "swelling" of the nanowire, thus bridging the nanogap breakjunctions (nanobreakjunctions) and leading to an overall decrease in the resistance along the length of the nanowire. The resistance change that occurs is between 6 and 8 orders of magnitude (typical devices see $1 \times 10^{-11}$ amps in the "off" state, and $1 \times 10^{-4}$ amps in the "on" state). This behavior is unique to nanowires possessing such nanogap breakjunctions. Fortunately, for sensor applications, these gaps re-open when the nanowires are removed from the hydrogen-containing environment, and the swollen nanowires revert back to their pre-swollen state.

The above-mentioned nanowire sensors have three primary deficiencies which can be improved upon. The first deficiency is the reliance on terraced graphite step ledges to form the nanowires. This limits the ability to pattern the nanowires into an arrangement of one's own choosing, i.e., it limits the length and orientation of the nanowires. The second deficiency lies with the need to transfer the nanowires from the conducting graphite surface to an insulating glass substrate using a cyanoacrylate "glue." Such transfer steps could damage the nanowires. Lastly, there are hydrogen concentration and temperature constraints which present, perhaps, the greatest deficiency in the prior art. At 25° C., for example, there is no $H_2$ concentration range over which this sensor can detect merely a 2% threshold. By 50° C., this threshold moves up to 4–5% $H_2$ in air, which is above the lower explosive limit. Consequently, such nanowire sensors essentially provide only a hydrogen detection capability within a very narrow temperature range, wherein such sensors essentially operate as simple on/off switches.

As a result of the foregoing, there is a need for a method that permits the ordered patterning of nanowires on a surface in a predefined way, and for a method that eliminates the need for the nanowires, once formed, to be transferred to another substrate. There is also a need for a method that overcomes the temperature/threshold concentration limitations of current hydrogen sensors and allows for a range of $H_2$ concentrations to be determined at any given temperature, and which allows for a wider range of operating temperatures such that the sensor is capable of detecting $H_2$ below its lower explosive limit. Such a device could be either a variable- or continuous-range hydrogen sensor.

SUMMARY OF THE INVENTION

The present invention provides for novel hydrogen sensors and methods for making same. Generally, such sensors comprise metal alloy nanostructures (wires, particles, films) having nanobreakjunctions that close when exposed to a certain level of hydrogen. Such sensors overcome many of the limitations of the prior art in that they can operate at much higher temperatures below the LEL of $H_2$, and, in some embodiments, can cover ranges of $H_2$ concentrations. Additionally, the fabrication of the sensors of the present invention avoid having to transfer the sensor elements to another substrate.

In some embodiments, such novel hydrogen sensors are variable-range hydrogen sensors comprising one or more fabricated Pd—Ag (palladium-silver) nanowires—each wire having the same or a different Ag to Pd ratio—with nanobreakjunctions in them and wherein the nanowires have predefined dimensions and orientation. When the nanowires are exposed to $H_2$, their lattice swells when the $H_2$ concentration reaches a threshold value (unique to that particular ratio of Pd to Ag). This causes the nanobreakjunctions to close leading to a 6–8 orders of magnitude decrease in the resistance along the length of the wire and providing a sensing mechanism for a range of hydrogen concentrations.

In some embodiments, the variable-range hydrogen sensors described herein are made by the electrochemical, electroless, or vapor deposition of metal into photolithographically-generated and etched channels within a dielectric material and which span two electrodes, permitting the generation of nanowires formed in any desired orientation, length, or arrangement, and without the need to transfer them to an additional substrate. Dimensions, in this embodiment are limited only by the dimensional limitations of photolithographic techniques, e.g., the wavelength of the radiation used.

In some embodiments, such novel hydrogen sensors are continuous-range hydrogen sensors comprising Pd—Ag nanoparticles arrayed as nanowires or two-dimensional shapes on a resistive surface, wherein nanobreakjunction gaps exist between at least some of the nanoparticles. Such continuous-range hydrogen sensors are capable of measuring a wide range of hydrogen gas concentration over a wide temperature range. Unlike existing hydrogen sensors that experience a large change in resistance at a certain hydrogen concentration, the continuous-range hydrogen sensors of the present invention change resistance continuously over a broad range of hydrogen concentration. This continuous change varies slowly with hydrogen concentration and is predictable such that the continuous-range hydrogen sensor can be used to measure hydrogen concentration continuously from a few ppm to 40,000 ppm level or higher over a broad range of temperatures (e.g., −40° C. to +150° C.).

In some embodiments, the fabrication of a continuous-range hydrogen sensor comprises two general series of steps: (a) the fabrication of a resistive substrate comprising low-resistivity contact pads, and (b) electroplating Pd—Ag onto the resistive substrate such that the Pd—Ag is deposited as an array of nanoparticles. In some embodiments, the resistive substrate is lithographically patterned. In such embodiments, the nanoparticle arrays conform to the substrate pattern.

The hydrogen sensors of the present invention can find use in any application where the detection of hydrogen gas is important. The present invention extends the temperature range at which such sensors can be operated beyond that currently available, thereby extending the utility of such sensors. One exemplary application for such hydrogen sensors is in the monitoring of hydrocarbon breakdown (which leads to the evolution of hydrogen) in transformers. Other applications include the monitoring of hydrogen in any application utilizing a hydrogen fuel cell.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

In some embodiments, the present invention provides for a method of generating metal nanowires on a surface, wherein the nanowires are grown with predefined dimensions, compositions, and orientations. Such metal nanowires are termed "precisely-defined" herein. The present invention is also directed to a variable-range hydrogen sensor comprising one or more precisely-defined palladium-silver (Pd—Ag) nanowires of variable composition and possessing nanobreakjunctions which are closed at a composition-dependent hydrogen concentration threshold. In some embodiments, an array of such nanowires of differing composition is used. In such embodiments, the nanobreakjunctions close (in sequential fashion) as the concentration of $H_2$ is increased. Changes in an electrical property or properties (e.g., resistance) of these nanowires as a function of $H_2$ concentration present, permits the sensing of $H_2$ over a range of concentration. Such a variable-range sensor can even permit concentration determination when electrical responses of the sensor have been calibrated against known quantities of $H_2$. The precision with which this can be done is merely dependent upon the number of precisely-defined metal nanowires of different Pd:Ag ratios present in the sensor.

In some embodiments of the present invention, the precisely-defined nanowire sensors ("nanowire sensors") described herein are made by the electrochemical, electroless, or vapor deposition of metal into photolithographically-generated and etched channels within a dielectric material and which span two electrodes, permitting the generation of nanowires formed in any desired orientation, length, or arrangement, and without the need to transfer them to an additional substrate. Dimensions, in this embodiment are limited only by the dimensional limitations of photolithographic techniques, e.g., the wavelength of the radiation used.

Figure 1:
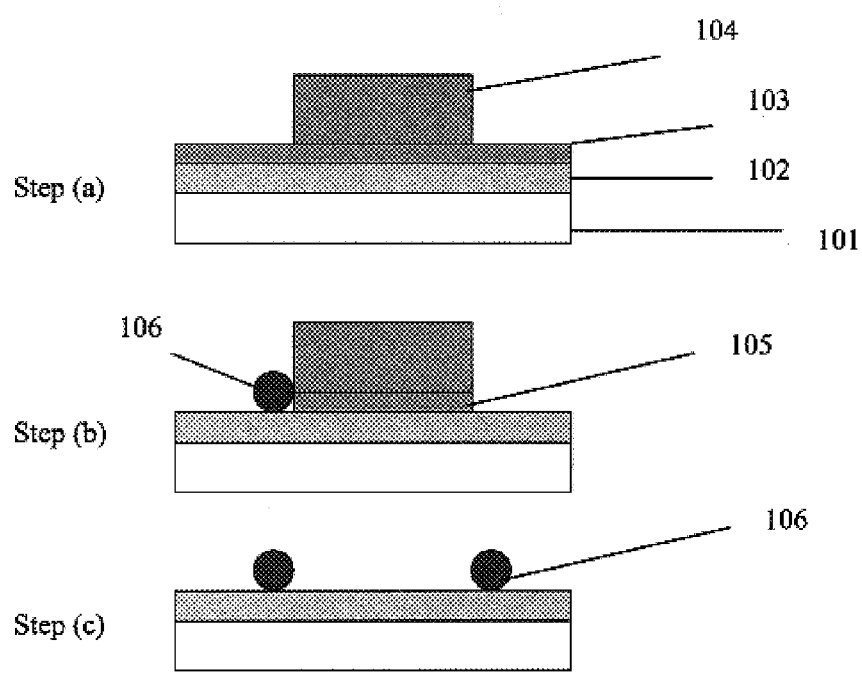
FIG. 1 illustrates an embodiment in which metal nanowires can be deposited on a substrate.

Referring to FIG. 1, in some embodiments, Pd nanowires are electrochemically deposited onto a $SiO_2$ dielectric substrate 102 (other embodiments employ different dielectric materials). In Step (a), a 200–600 nm thick layer of silicon dioxide ($SiO_2$) 102 is plasma deposited on top of the base Si substrate 101. On top of this, Ti is thermally evaporated and condensed onto the surface such that a 10–100 nm (e.g., ~50 nm) Ti film 103 resides on top of the $SiO_2$ (note that in other embodiments Ti is sputtered or electron-beam evaporated onto the surface). A 1–5 μm (e.g., ~2 μm) Shipley AZ photoresist (PR) layer 104 is spin-coated onto the Ti film 103 using a spin coater operating at about 1000–5000 RPM. A subsequent baking process is used to remove the solvent. A photomask (essentially a glass plate with a photo-opaque design on it) is applied to the PR layer 104 and is exposed to UV light (e.g., generated by a mercury arc lamp or other source). The photomask is removed and the substrate is placed in a developer which removes the UV-exposed regions of the PR layer 104, thus creating a pattern in the PR layer 104. In Step (b), the Ti layer 103 is etched using a reactive ion etching (RIE) plasma using a fluorine- or chlorine-containing gas (or other suitable etching process). This generates nanoscale "walls" (nanowalls) of Ti 105 which can then be electrically-biased such that Pd is electrochemically deposited (from a solution) along the Ti walls 105 as Pd nanowires 106 having diameters generally in the range of about 100 nm to about 700 nm, and perhaps smaller. Methods for electrochemically depositing Pd from solution are well known in the art (F. Favier, E. C. Walter, M. P. Zach, T. Benter, R. M. Penner "Hydrogen Sensors and Switches from Electrodeposited Palladium Mesowire Arrays," Science, 293, p. 2227–2231, 2001). In Step (c), the patterned photoresist 104 and the Ti walls 105 are removed to reveal the isolated nanowires 106. Variations on this embodiment include substituting carbon (C), tungsten (W), alloys of titanium and tungsten (TiW), and aluminum (Al) for the Ti, and electrochemically depositing nanowires of Pd-alloys like Pd—Ag. In this manner, nanowires of a variety of Pd:Ag ratios can be made.

Figure 2:
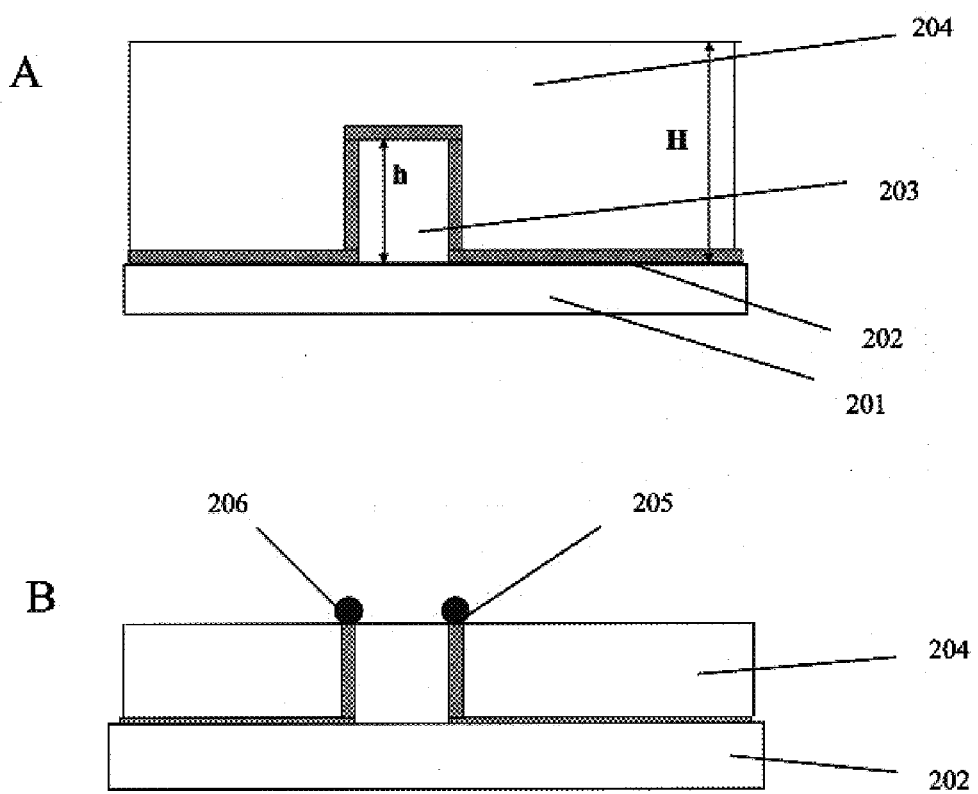
FIGS. 2A and 2B illustrate an embodiment wherein chemical mechanical etching is used to generate metal electrodes (embedded in a dielectric surface) on which Pd or Pd-alloy nanowires can be electrochemically grown.

In another embodiment, shown in FIG. 2, small rectangular structures 203 of height h are formed from a dielectric material, e.g., $SiO_2$. These structures are placed on a surface 201, covered with a thin (~10 nm thick) metal layer 202 (e.g., Ni), then planarized with additional dielectric 204 to height H, as shown in FIG. 2A. Chemical-mechanical polishing (CMP) is then employed to etch away the dielectric material (from height H to below height h) and exposes the metal electrodes 205 on which the Pd or Pd-alloy nanowires 206 are grown, as shown in FIG. 2B. Variations on this embodiment include different dielectric materials, different metal thin films, size and shape of the dielectric structures, and where and how they are placed on the surface.

In another embodiment, polymethylmethacrylate (PMMA), or other suitable electron-beam resist material, is deposited on a conductive metal which has itself been deposited on a $SiO_2$ surface (or the surface of any dielectric material). Electron-beam (e-beam) lithography is then used to generate lines in the PMMA which can be as small as 20 nm in width. The conductive metal is then etched (via a RIE process) to replicate the PMMA pattern in the metal. The PMMA is removed and Pd or a Pd-alloy is electrodeposited onto the surface. The conductive metal can be optionally removed to maximize the performance of the hydrogen sensor.

One conductive "metal" ideally suited to the application described in the preceding embodiment is carbon. In some embodiments, deposition of the PMMA onto a carbon-coated dielectric surface, lithographically patterning the PMMA with an electron beam, reactive ion etching of the exposed carbon, and removal of PMMA yields carbon nanoelectrodes along which Pd and Pd-alloy nanowires are grown. The carbon is then removed via RIE in either a hydrogen, oxygen, or air plasma. The carbon leaves as a volatile reaction product like methane ($CH_4$), carbon monoxide (CO), or carbon dioxide ($CO_2$)—depending on which reactive ion etch is used.

In another embodiment, PMMA is deposited directly onto an $SiO_2$ surface (or the surface of any dielectric material). Electron-beam lithography is then used to generate channels in the PMMA which can be as small as 20 nm in diameter. Pd or a Pd-alloy is then electrolessly-deposited onto the surface. Finally, the PMMA is removed with a suitable solvent to leave free-standing Pd or Pd-alloy nanowires on the surface.

In other embodiments of the present invention, carbon nanotubes (CNTs) are plated with a thin film of Pd or Pd-alloy using either an electrochemical or electroless plating process. Such thin films possess the same nanobreakjunctions that the other nanowires described herein do along the length of the CNTs. The underlying carbon (i.e., the carbon nanotubes) in these coated nanotubes is then removed via reactive ion etching, as described in the preceding paragraph, to yield Pd or Pd-alloy nanowires. In some of the embodiments utilizing carbon nanotubes, the CNT is grown in situ between two electrodes using an established vapor growth mechanism. Such a process, leads to the formation of some of the smallest Pd and Pd-alloy nanowire hydrogen sensors (CNTs can have diameters as small as 0.5 nm, but CNTs grown from a supported catalyst structure are usually larger). In other embodiments, the CNTs are produced external to the sensor device, then they are coated with Pd or a Pd-alloy. Such coated CNTs are then dispersed on a surface or in lithographically-generated channels bridging two electrodes on a surface. In these latter embodiments utilizing CNTs, the nanowire sensor is actually composed of a number of smaller nanowires.

Other embodiments of the present invention involve coating nanoparticles (having diameters as small as 1 nm) with a Pd and Pd-alloy. Silicon, silica, diamond, alumina, titania, or any other nanoparticle material is electrolessly plated with a Pd or Pd-alloy. These coated nanoparticles are then applied to a surface and made to bridge two electrodes using electrophoresis, spray methods, or pastes. Nanobreakjunctions exist in the coated surfaces and in the gaps (nanogaps) between adjacent particles. Variations on these embodiments include depositing such coated nanoparticles within lithographically-patterned channels on the surface of a dielectric material, and generating nanoparticles of Pd and Pd-alloys electrochemically on a surface.

In some embodiments involving nanoparticles, the nanoparticles are deposited or applied to a surface in such a way so as to assure that there is significant contact between nanoparticles. This ensures that electrical contact is made throughout the entire nanoparticle network. As in the electrochemically-generated Pd and Pd-alloy wires, it is often the nanobreakjunctions on the surface of the coated particles which serve in the sensing mechanism. Here, the nanowires are simply created with numerous coated nanoparticles.

Other embodiments include depositing Pd and Pd-alloys using thermal- or electron-beam evaporation. Furthermore, nanowires of any platable metal or combination of platable metals can be made using either electrochemical or vapor deposition techniques. Platable metals include, but are not limited to, Ag, Au, Cu, Co, Fe, Ni, Pd, Pt, Cr, Zn, Sn, Ti, and combinations thereof. As will be appreciated by those of skill in the art, countless other variations exist utilizing maskless or laser photolithographic techniques and combinations of all the previously mentioned techniques.

The nanowires of the present invention can also be patterned on a surface to have specific dimensions and orientations. This is important because future commercialization of this technology will likely depend on the ability to control the size, shape, and orientation of the nanowires within a manufacturing context.

The above-described processes of making metal nanowires provide numerous advantages over the existing prior art, particularly for fabricating hydrogen sensors. The number, length, diameter, and orientation of nanowires in the device can all be controlled by lithography. The electroplating (deposition) process can be more easily controlled because one knows exactly the length and number of wires and therefore can control the size of the nanowires more easily. All the nanowires can be aligned in parallel (if desired), whereas the prior art does not have any control over this on a graphite surface. Much of the technology of the present invention is built on Si which is easily cleaved/sawed into individual devices, rather than being on glass which is difficult to work with. Furthermore, no glue (cyanoacrylate) is required in the processes of the present invention. Such glue has limited use over a temperature range, and typically has a thermal coefficient of expansion which may further limit its use over a range of temperatures.

In general, the present invention also comprises any method that allows for the creation and controlled placement of Pd and Pd-alloy (e.g., Pd—Ag) nanowires for use as hydrogen sensors. The invention also provides for variable-range hydrogen sensors in that it provides a method for preparing nanowires which are sensitive to hydrogen over a range of concentrations at a given temperature and to a given $H_2$ concentration over a range of temperatures. This is accomplished by alloying the Pd with Ag and forming nanowires of this Pd—Ag alloy as described above. Like the Pd nanowires, such Pd—Ag nanowires possess nanobreakjunctions which are responsive to $H_2$ concentration. Alloying Pd with Ag permits one to modulate the α-β transition and enables the sensor to respond (by closing the nanobreakjunctions) to a much wider range of temperatures and $H_2$ concentrations. Methods of electrochemically (J. N. Keuler, L. Lorenzen, R. D. Sanderson, V. Prozesky, W. J. Przybylowicz "Characterization of electroless plated palladium-silver alloy membranes," Thin Solid Films, 347, p. 91–98, 1999) and evaporatively (V. Jayaraman, Y. S. Lin "Synthesis and hydrogen permeation properties of ultrathin palladium-silver alloy membranes," J. Membrane Sci., 104, p. 251–262, 1995) alloying Ag with Pd are well-established. The invention also provides a method of making sensors comprising an array of several (2 or more) metal nanowires, each possessing a different Pd/Ag ratio, where the amount of Ag can vary from about 0% to about 40%. Not intending to be bound by theory, other platable metals and combinations of platable metals may also be used to make nanowire sensors for hydrogen and, perhaps, other gases. The key here is that such nanowires comprise nanobreakjunctions which close at some threshold hydrogen concentration.

Figure 3:
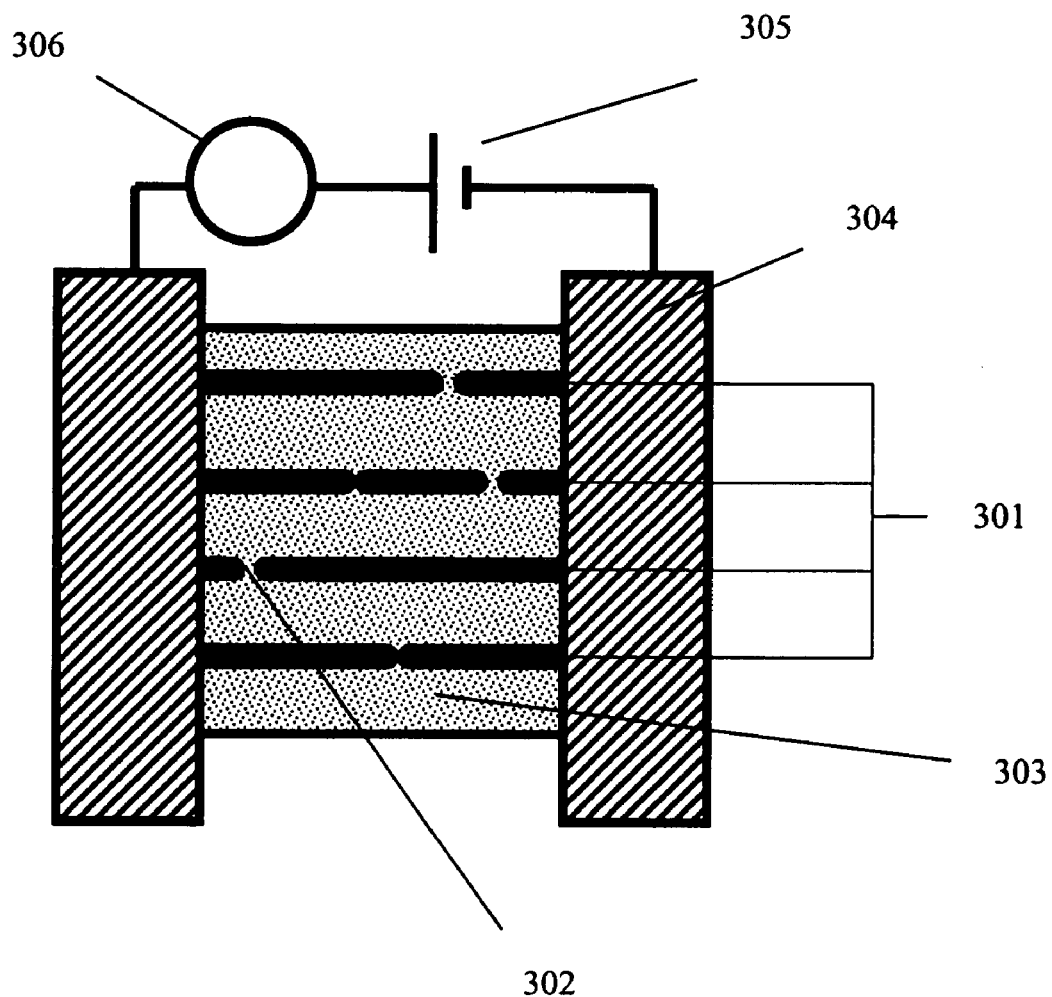
FIG. 3 illustrates a variable-range hydrogen sensor of the present invention comprising metal nanowires.

FIG. 3 illustrates a variable-range hydrogen sensor of the present invention comprising metal nanowires. Referring to FIG. 3, metal alloy nanowires 301 of variable composition and comprising nanobreakjunctions 302 are present on a dielectric surface 303. An electric circuit comprising the nanowires 301 is formed with electrical contacts of metal film 304 and a power supply 305. The sensor functions by monitoring some electrical property of the nanowires with a monitoring device 306 (e.g., an amp meter) for changes as the nanowires are exposed to hydrogen.

Figure 4:
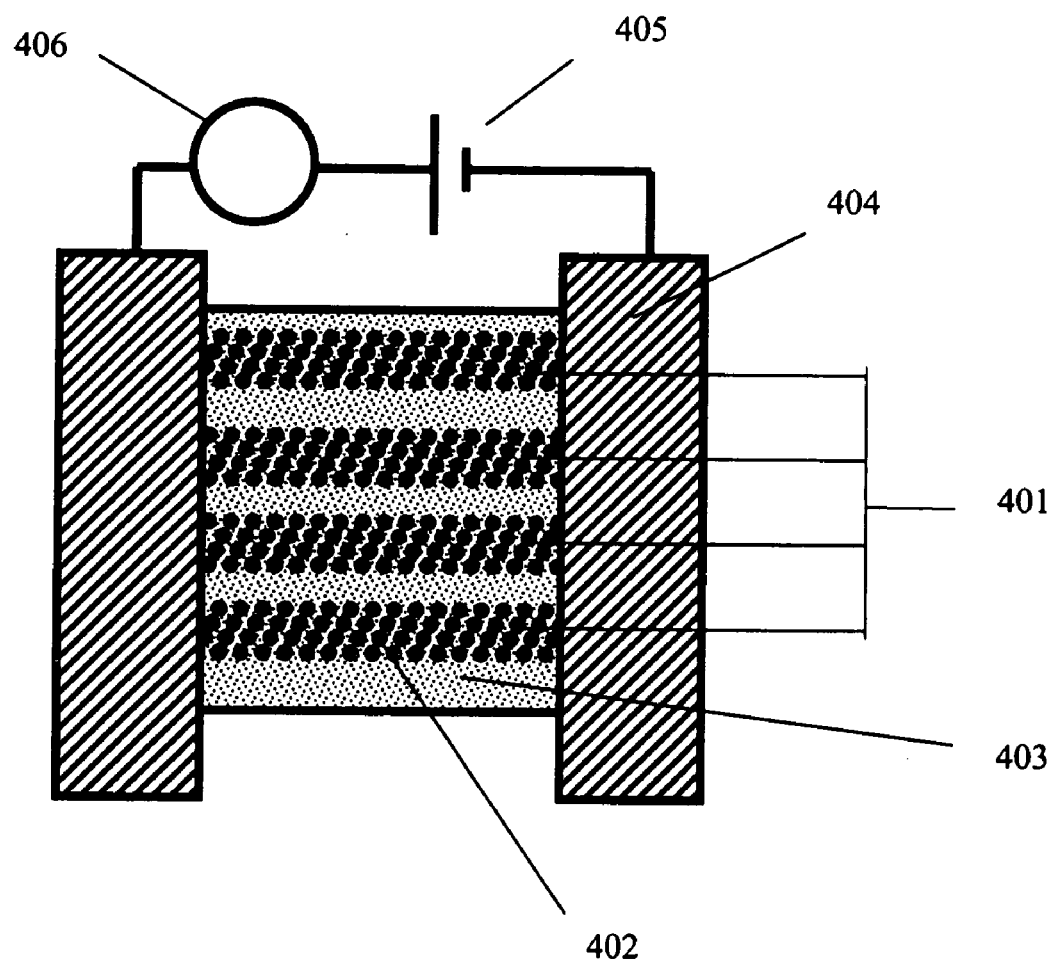
FIG. 4 illustrates a variable-range hydrogen sensor of the present invention comprising columns of metal nanoparticles.

FIG. 4 illustrates a variable-range hydrogen sensor of the present invention comprising columns of metal nanoparticles. Referring to FIG. 4, columns of metal alloy nanoparticles 401 of variable composition and comprising nanobreakjunctions and nanogaps 402 are present on a dielectric surface 403. An electric circuit comprising the columns of metal alloy nanoparticles 401 is formed with electrical contacts of metal film 404 and a power supply 405. The sensor functions by monitoring some electrical property of the nanowires with a monitoring device 406 (e.g., an amp meter) for changes as the columns of nanoparticles are exposed to hydrogen.

An advantage to alloying Pd with Ag in the nanowires is that it permits the formation of hydrogen sensors having a variable-range of detection points. Using pure Pd nanowires, one is limited only to about a 2% detection capability at room temperature, and at 40–50° C., the α-β transition point shifts to 4–5% $H_2$, above the point at which it is useful in detecting explosive $H_2$ levels. This limitation is overcome by making nanowire alloys of Pd—Ag in the 0–40% weight concentration of Ag to Pd. As mentioned above, such nanowire alloys will permit hydrogen detection over a wide range of temperatures and hydrogen concentrations. Furthermore, using an array of different Pd—Ag nanowires (multiple nanowires, each having a different Pd to Ag ratio) allows for the formation of a variable-range hydrogen sensor which will be dramatically more useful in research and industrial settings.

Additionally, as an alternative to basing the sensing mechanism on a sharp change in resistance, the hydrogen sensing process can also be made to work on changes in capacitance or conductance. Essentially, monitoring any electrical property which changes in a pre-defined manner as a result of closing the nanobreakjunctions within the nanowire can be used to sense an increase in the hydrogen concentration of the surrounding environment.

In some embodiments, such novel hydrogen sensors are continuous-range hydrogen sensors comprising Pd—Ag nanoparticles arrayed as nanowires or two-dimensional shapes on a resistive surface, wherein gaps (nanobreakjunction gaps) between the particles approximate the breakjunctions described above. Generally such nanoparticles have diameters on the order of 1–100 nm, and typically 5–50 nm. Such continuous-range hydrogen sensors are capable of measuring a wide range of hydrogen gas concentration over a wide temperature range. Unlike existing hydrogen sensors that experience a large change in resistance at a certain hydrogen concentration, the continuous-range hydrogen sensors of the present invention change resistance continuously over a broad range of hydrogen concentration. This continuous change varies slowly with hydrogen concentration and is predictable such that the continuous-range hydrogen sensor can be used to measure hydrogen concentration continuously from a few ppm to 40,000 ppm level or higher over a broad range of temperatures (e.g., −40° C. to +150° C.).

Figure 5:
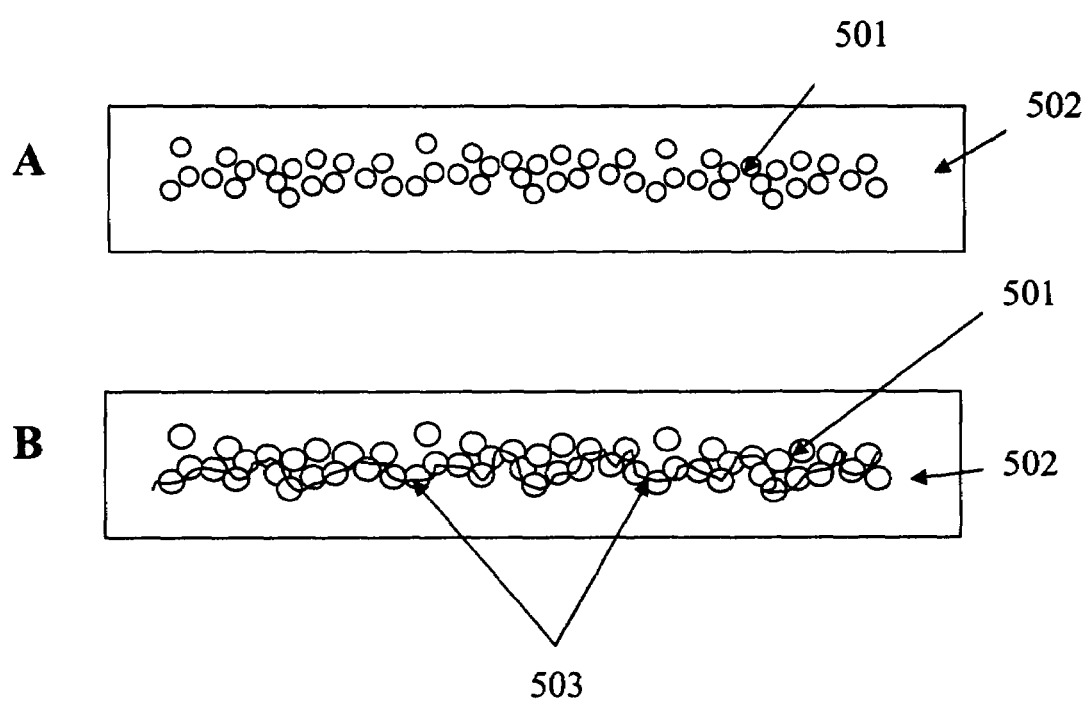
FIGS. 5A and 5B illustrate how existing Pd nanoparticle-containing hydrogen sensors operate.

The existing prior art concept of threshold level hydrogen sensor/detector is illustrated in FIGS. 5A and 5B. Referring to FIG. 5A, palladium nanoparticles 501 (the circles in the figure) are sitting, as a film, on an insulating substrate 502. See United States Patent Application No. 2003/0079999. If the hydrogen level is below the threshold, there is no electrical path between one end of the film and the other; the resistance is very high. If the sensor film in placed in a hydrogen atmosphere with a hydrogen concentration above the threshold, as shown in FIG. 5B, then an electrical path 503 is formed from one end of the film to the other, and the resistance drops dramatically. This is analogous to an on/off switch.

Figure 6:
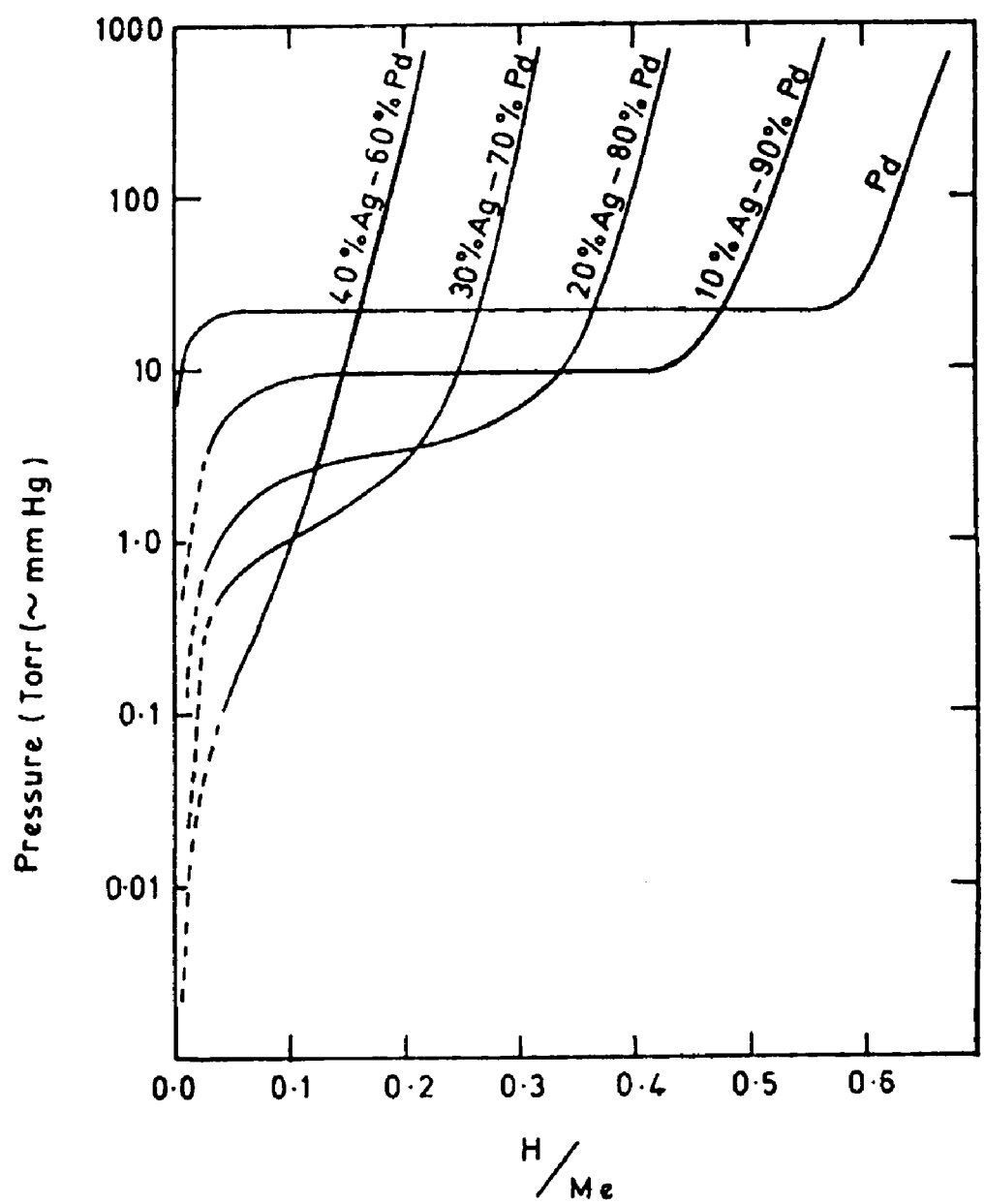
FIG. 6 depicts p-C isotherms for various Pd—Ag alloy compositions at 50° C.
Figure 7:
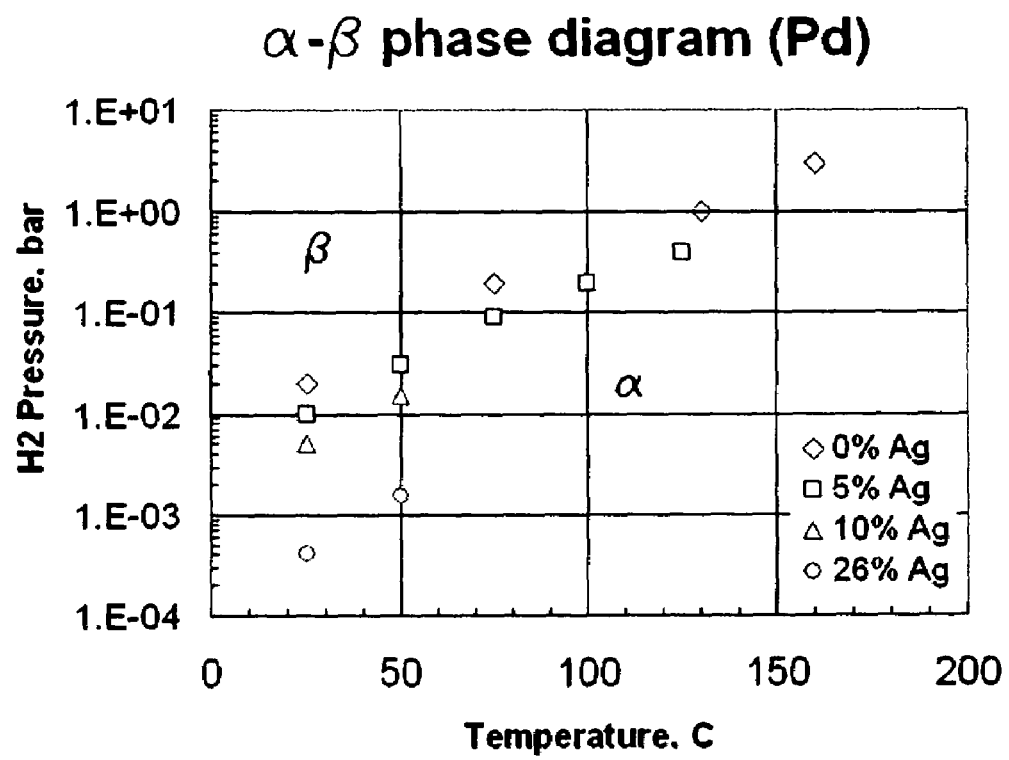
FIG. 7 depicts p-T relationships for Pd—Ag alloys at phase transition.

The continuous-range hydrogen sensors of the present invention have several distinguishing attributes that differentiate them over the prior art sensors described above. First, the Pd nanoparticles are alloyed with other metals. In particular, Ag metal is used since it increases the temperature range over which the nanoparticles will change phase. Such alloying also makes the lattice constant change over a continuous-range of hydrogen concentrations and temperatures; it is not abrupt like the sensors of the prior art. Additionally, smoother phase transitions are observed for alloys with higher Ag content, as shown in FIG. 6, which depicts p-C isotherms for Pd—Ag alloys at 50° C., and in FIG. 7, which depicts p-T relationships for Pd—Ag alloys at phase transition. Second, the concentration of Ag or other metals in the nanoparticles used in the present invention may be different from particle to particle. This means that some particles will start expanding at a certain concentration range of hydrogen and other particles will not be affected until the film is put into even higher levels of hydrogen concentration. Third, the continuous-range hydrogen sensors of the present invention typically have the Pd-alloy nanoparticles sitting on a resistive surface (such as titanium (Ti)), as opposed to a completely insulating substrate. In this case, the surface of the substrate, or the substrate itself, provides some level of conductivity from one end of the sensor to the other. Generally, any metal or combination of metals that undergo an $\alpha$ to $\beta$ phase change that expands the metal lattice and closes the nanobreakjunction gaps will work.

Figure 8:
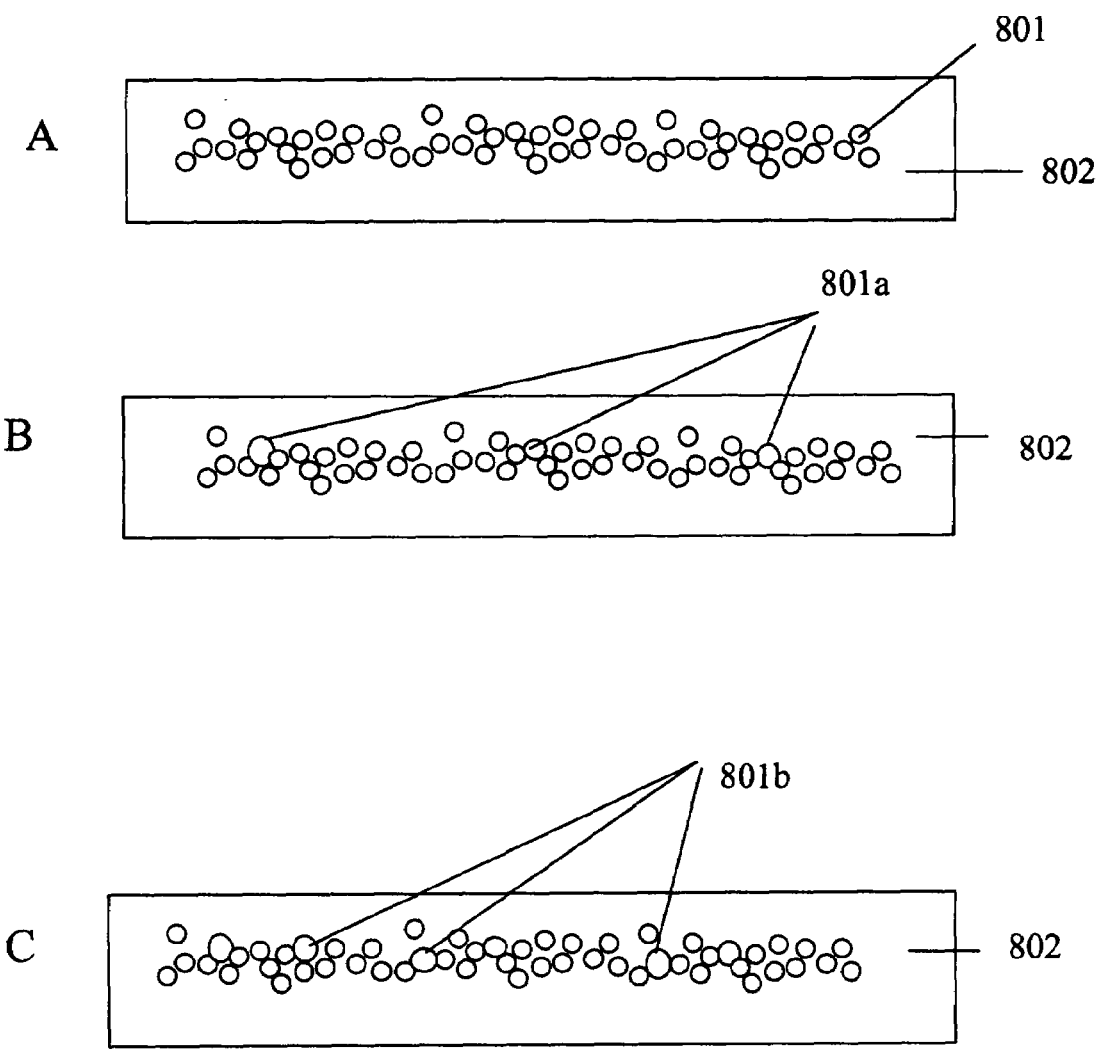
FIGS. 8A–8C depict the operation of a continuous-range hydrogen sensor of the present invention.

FIGS. 8A–8C depict the operation of a continuous-range $H_2$ sensor of the present invention. Referring to FIG. 8A, Pd—Ag nanoparticles 801 sit under low-$H_2$ concentration conditions, as a film, on resistive substrate 802. In some embodiments, the resistive substrate comprises Ti. In FIG. 8B, the hydrogen concentration has been increased causing some particles 801a, having certain Pd—Ag ratios, to increase in size. As a result, resistance has decreased because some contacts have been made which have shorted the resistive surface in the region of the contacts. As the hydrogen concentration is increased further, as in FIG. 8C, additional nanoparticles 801b, having other Pd—Ag ratios, increase in size and cause electrical shorts which decrease the electrical resistance of the nanowire (array or film of nanoparticles) in an incremental manner from one end of the wire (film) to the other, because each nanoparticle contact with other nanoparticles electrically shorts the resistive film that the nanoparticles are sitting on. In practice, there are a range of nanoparticle compositions (varying from nanoparticle to nanoparticle) in the nanowire, such that the resistance is decreasing in a continuous manner.

Figure 9:
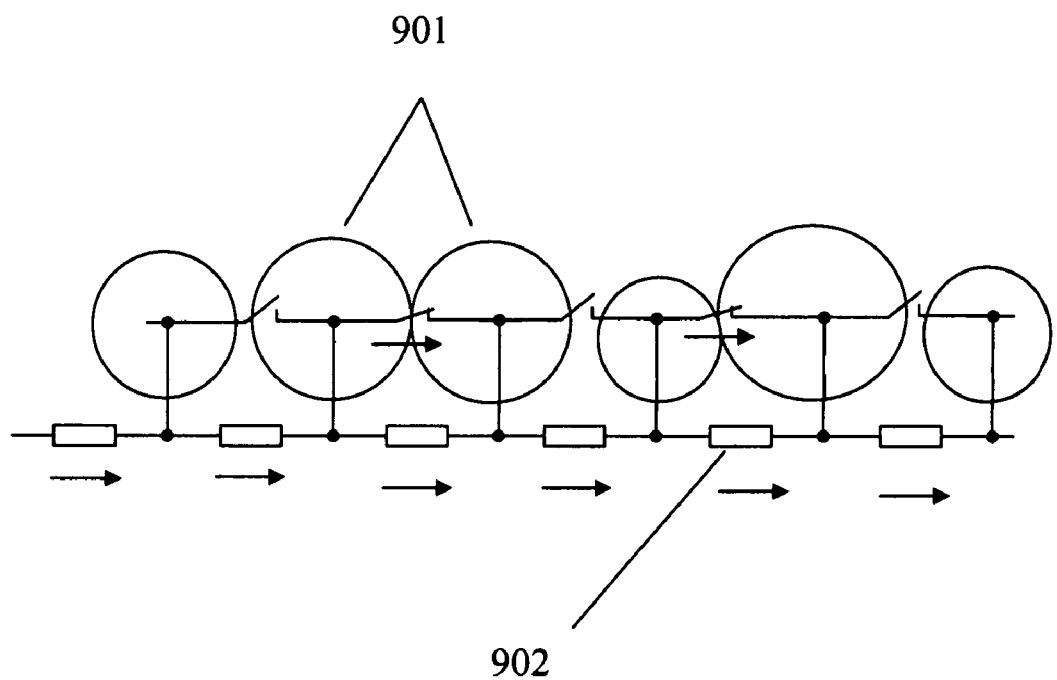
FIG. 9 illustrates, in an electrical circuit schematic, the continuous-range hydrogen sensor operation depicted in FIGS. 8A–8C.

The above-described process can also be shown in an electrical circuit schematic, as shown in FIG. 9, wherein arrows show the direction of the current flow and resistors 902 represent the substrate. Particles 901 expand to fill nanobreakjunction gaps as hydrogen concentration increases.

Accordingly, Applicants have created hydrogen sensors that sense hydrogen over a continuous range. The alloying of the Ag with Pd forces the lattice constant of the alloy to change continuously with hydrogen concentration. Additionally, each nanoparticle need not have the same Ag:Pd alloy ratio, so each nanoparticle may expand and contract differently as the hydrogen concentration levels are changed. Furthermore, there is no reliance on the nanoparticle film itself to make a continuous electrical circuit, but only that certain parts of the nanoparticle network make high conductivity segments that short out the resistive film or substrate on which the particles reside.

In some embodiments, the fabrication of a continuous range hydrogen sensor comprises two general series of steps: (a) the fabrication of a resistive substrate (surface) comprising low-resistivity contact pads and typically having a pre-defined shape or area, and (b) electroplating Pd—Ag onto the resistive substrate such that the Pd—Ag is deposited as an array of nanoparticles. In some embodiments, the resistive substrate is lithographically patterned. In such embodiments, the nanoparticle arrays conform to the substrate pattern.

Figure 10:
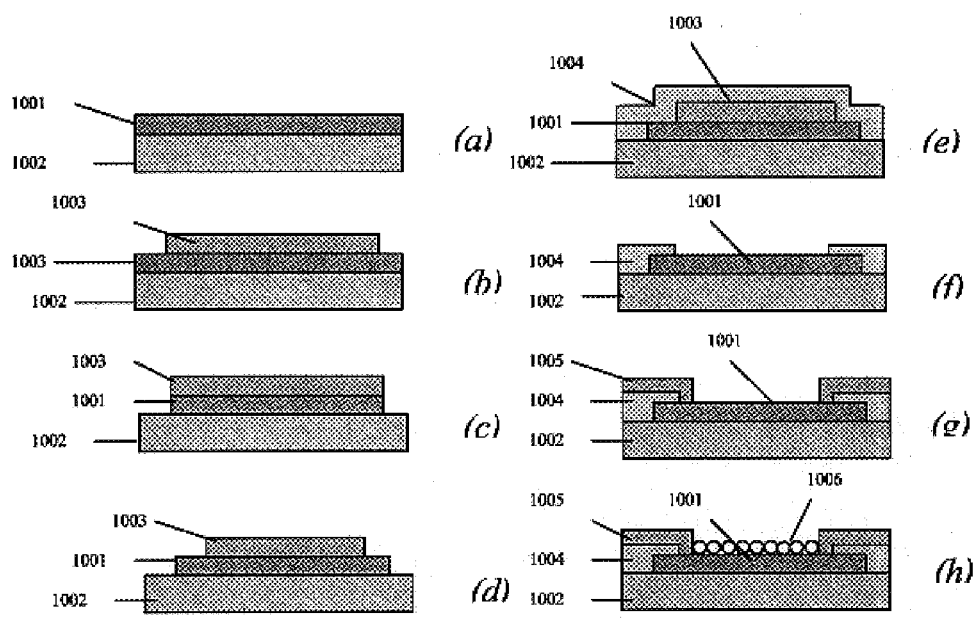
FIG. 10 schematically illustrates the stepwise fabrication of a resistive substrate for use in a continuous-range $H_2$ sensor.

Referring to FIG. 10, in fabricating a resistive substrate, a resistive layer 1001 of titanium (or other suitable resistive material) with a thickness of ~100 Å is deposited on an insulating substrate 1002, e.g., a glass wafer, as shown in Step (a). After making a Ti sensor pattern (Steps (b) and (c)) and stripping the photoresist 1003, another layer of photoresist 1003 is applied for patterning contact pads, as shown in Step (d). An ~500 Å layer 1004 of low-resistivity metal, such as gold, is then deposited over the Ti to make the contact pads, as shown in Step (e). A subsequent photoresist lift-off process (Step (f)) exposes the Ti sensor pattern. After that, a protective layer of photoresist 1005 is coated over the wafer such that after developing, open areas are created above the Ti sensor pattern (Step (g)) to ensure electroplating of Pd—Ag nanoparticles 1006 on the Ti surface, as shown in Step (h).

Figure 11:
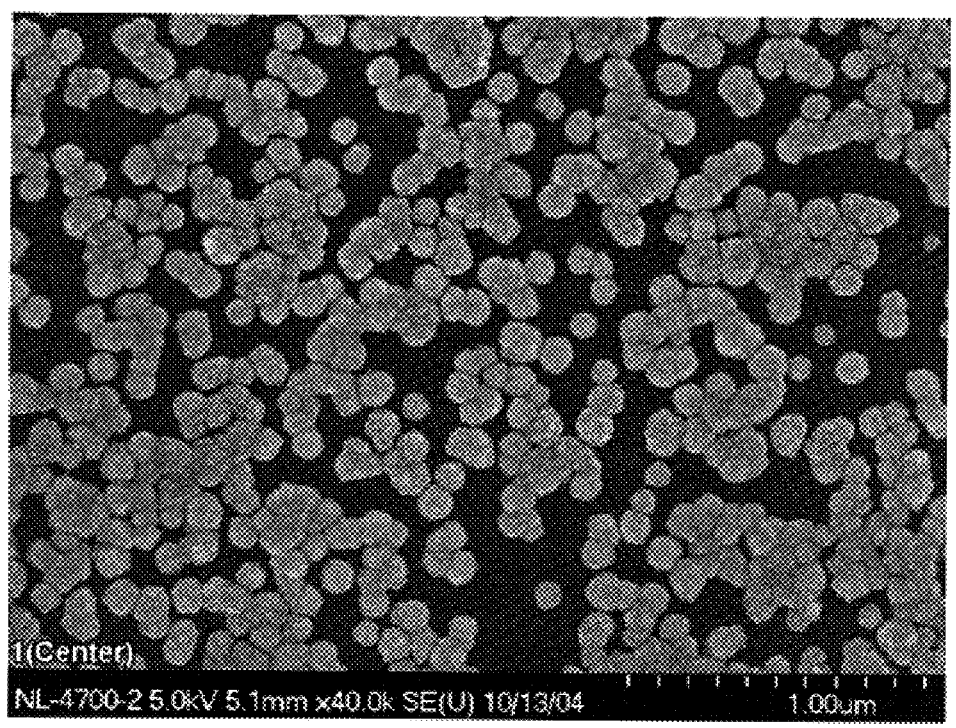
FIG. 11 is an SEM image depicting an electroplated array (film) of Pd—Ag nanoparticles.
Figure 12A:
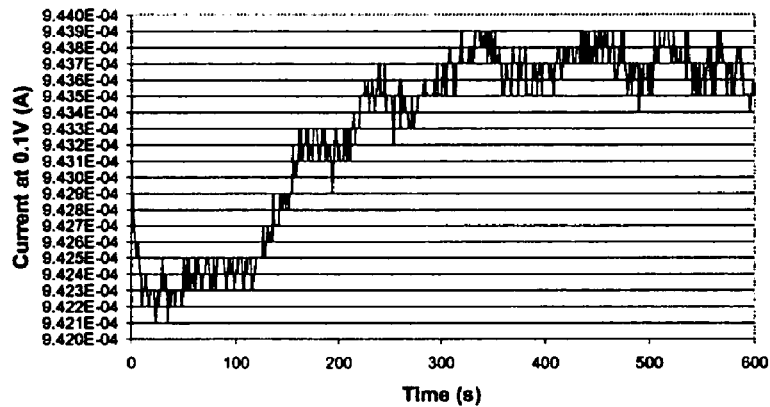
FIGS. 12A–12D illustrate the response of a continuous-range $H_2$ sensor to hydrogen dissolved in oil at different concentrations: (A) 22 ppm, (B) 148 ppm, (C) 419 ppm, and (D) 1323 ppm.
Figure 12B:
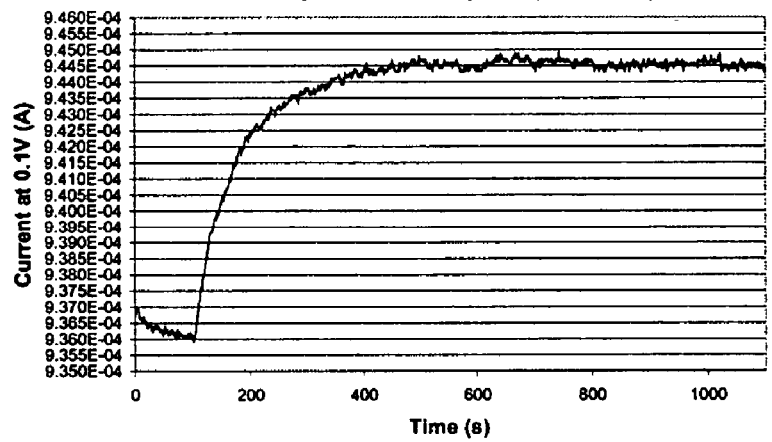
Figure 12C:
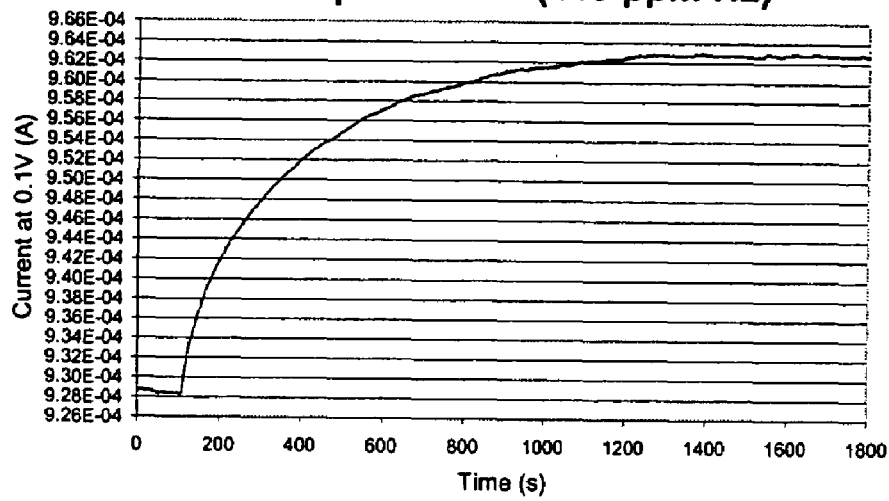
Figure 12D:
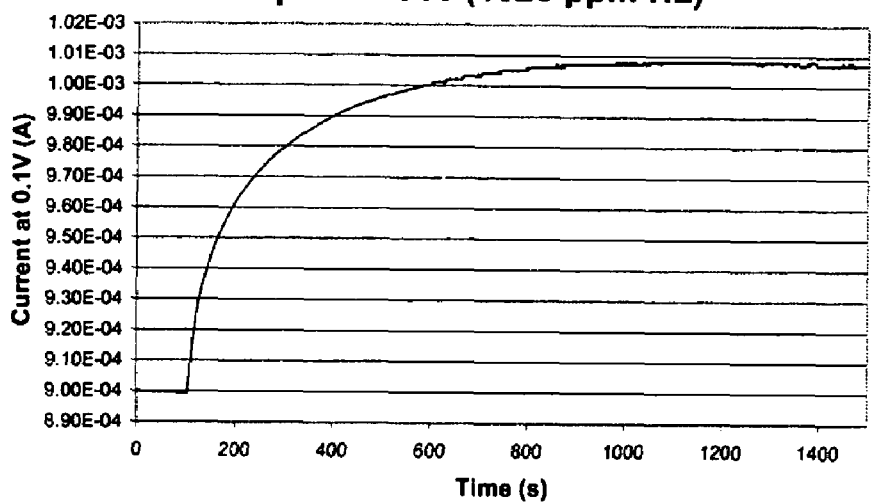

After substrate fabrication, the next series of steps involved in making a continuous range hydrogen sensor of the present invention is electroplating the patterned substrate with a layer of nanoparticles (Step (h) above). In this series of steps, an aqueous solution comprising Pd and Ag salts and other components is prepared and used as a plating bath. A series of pulsed currents is then applied to the sensor substrate. The currents and times may vary depending on the substrate area and design. FIG. 11 is a scanning electron microscopy (SEM) image depicting an electroplated layer of nanoparticles on a substrate, wherein the nanoparticles are about 10 nm in diameter.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

This example illustrates the electroplating of Pd—Ag nanoparticles onto a patterned substrate to make a continuous-range $H_2$ sensor in accordance with some embodiments of the present invention.

First, an aqueous Pd—Ag plating bath (solution) was made comprising 2.5 mM $PdCl_2$, 0.5 mM $AgNO_3$, 0.05 M $NaNO_3$, 0.05 M HCl, and 2 M NaCl. The ratio of Pd to Ag in this bath is 5:1. The order in which the bath components are mixed can be important. Accordingly, the components were mixed in the following order: 1) $AgNO_3 \rightarrow$ 2) $NaNO_3 \rightarrow$ 3) water $\rightarrow$ 4) HCl (solution should be milky in appearance due to the formation of AgCl)→5) NaCl until the solution becomes clear→6) $PdCl_2$.

Next, an electroplating process was carried out using chronopotentiometry (constant current process) in a three electrode system to electrochemically deposit nanoparticles onto a patterned Ti substrate. Conditions for electroplating were as follows: −300 μA for 5 seconds (nucleation step), then −20 μA for 450 seconds (growth step) for an area of 15 $mm^2$ Ti exposed to the plating solution. This corresponds to current densities of about 2 $mA/cm^2$ for the nucleation step and 0.14 $mA/cm^2$ for the growth. The electrochemical conditions can be varied for different substrate materials and plating areas. Different Pd:Ag alloy compositions can be achieved by using different ratios of Pd and Ag salts in the plating solution.

EXAMPLE 2

This example illustrates how a continuous-range hydrogen sensor of the present invention can be used in the sensing of hydrogen gas.

Figure 13:
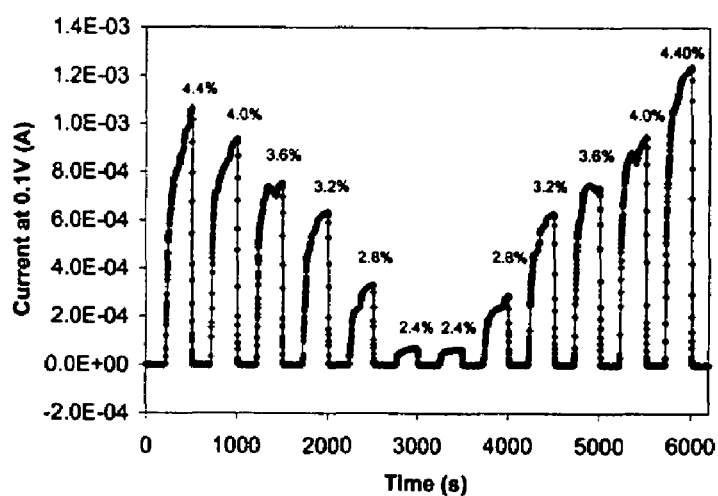
FIGS. 13A and 13B illustrate the response of a continuous-range $H_2$ sensor to varying $H_2$ concentrations in air.
Figure 13:
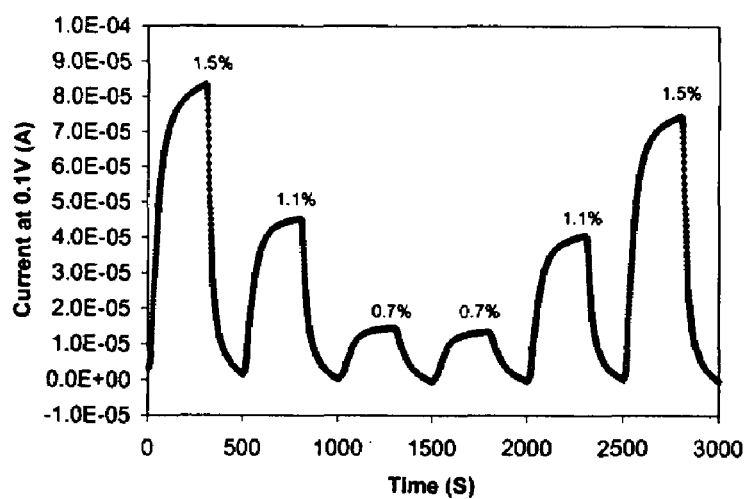

The results of such a sensor measuring the hydrogen concentration dissolved in oil are shown in FIGS. 12A–12D. FIGS. 12A–12D show the response of the hydrogen sensor to hydrogen dissolved in oil at different concentrations (22 ppm, 148 ppm, 419 ppm, 1323 ppm) at room temperature. In all cases the response time of the sensor was around 10 minutes. The same results can be seen when measuring the hydrogen concentration in air, as illustrated in FIGS. 13A and 13B which show the response of a sensor to hydrogen in at different concentrations below the LEL: 2.4–4.4% (FIG. 13A) and 0.7–1.5% (FIG. 13B). The measurements were done at the temperature of 70° C.

EXAMPLE 3

This example illustrates applications in which the hydrogen sensors of the present invention find utility.

Figure 14:
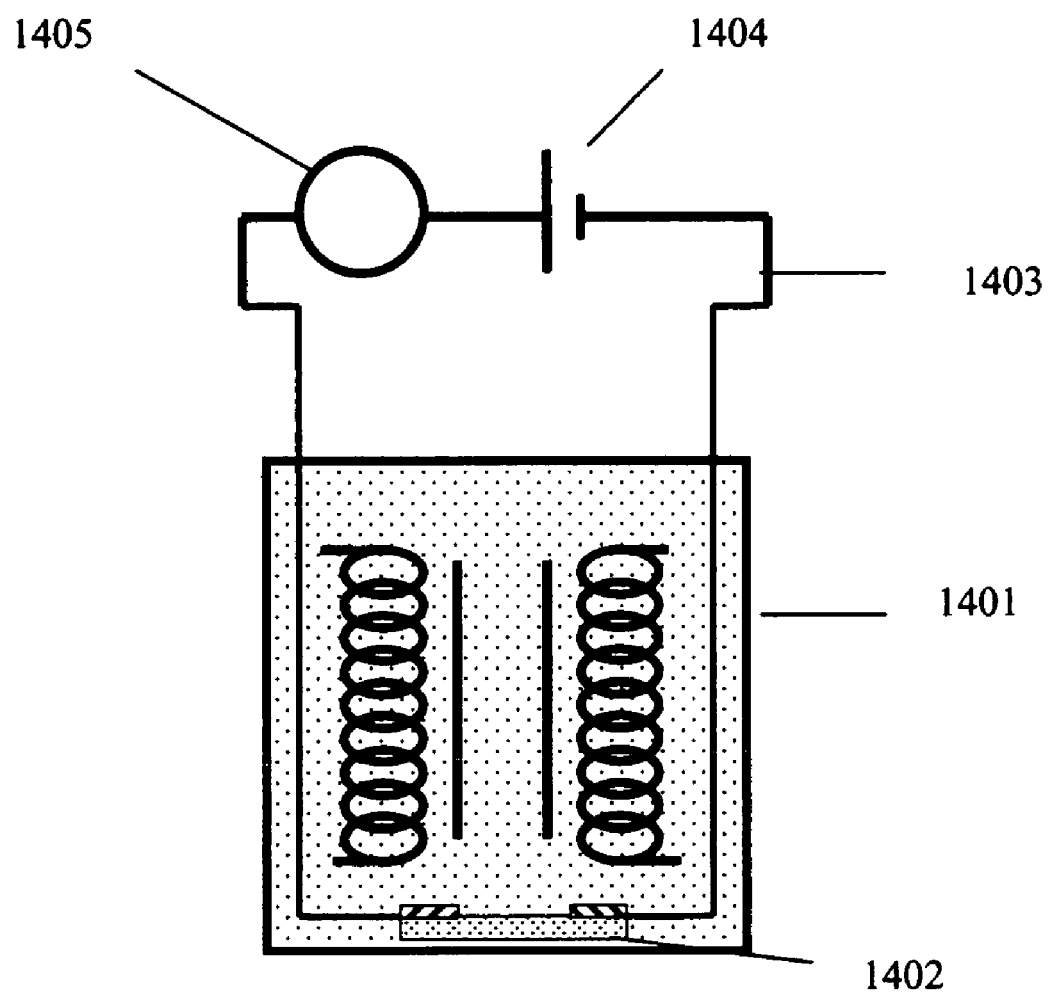
FIG. 14 illustrates the placement of a $H_2$ sensor of the present invention in a transformer to monitor for hydrocarbon breakdown.

An exemplary application for such hydrogen sensors is in the monitoring of hydrocarbon breakdown (which leads to the evolution of hydrogen) in transformers. FIG. 14 illustrates a placement of such a sensor 1402 in a transformer 1401 for hydrogen monitoring, wherein electrical contacts 1403 connect the sensing element 1402 (comprising nanowires or columns of metal nanoparticles) to a power supply 1404 and an electrical property monitoring device 1405. In some embodiments, the sensor 1402 is placed in the transformer such that it is exposed to transformer oil. When the filled transformer operation becomes defective, hydrogen and other dissolved gases form in the oil. The sensor 1402 monitors the $H_2$ content dissolved in the oil, helping to identify potential breakdowns and permitting maintenance before such breakdown occurs. Such monitoring can serve to economize the maintenance and downtime involved in operating such transformers by providing for a realtime and remote monitoring means.

Figure 15A:
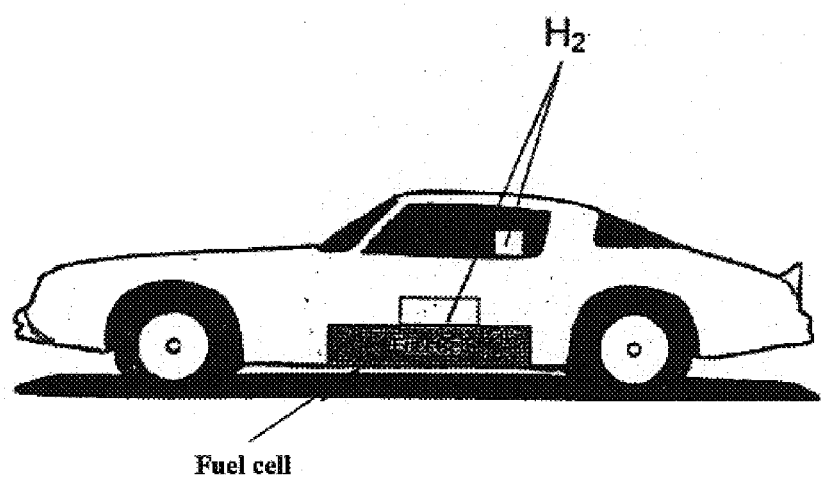
FIGS. 15A and 15B illustrate the use of hydrogen sensors of the present invention in applications utilizing hydrogen fuel cells, such as automobiles (A) and residential housing (B).
Figure 15B:
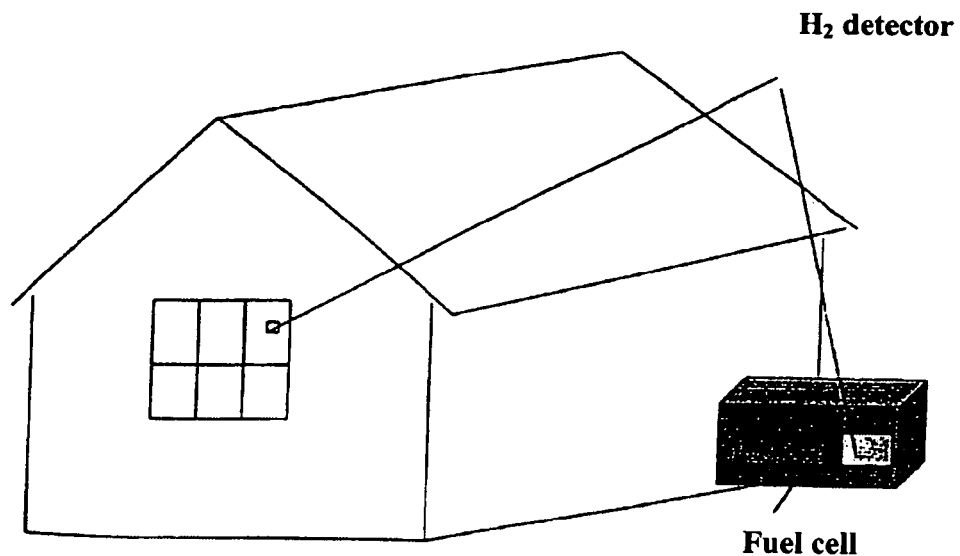

Other application for such sensors include any application utilizing a hydrogen fuel cell, where such a fuel cell could potentially leak flammable hydrogen gas. FIG. 15A depicts such an application, wherein a hydrogen sensor is placed in a hydrogen fuel cell-powered automobile. FIG. 15B depicts another such application, wherein a hydrogen sensor is employed to detect potentially explosive levels of hydrogen gas in a house or residence that utilizes a hydrogen fuel cell.

Although the present invention and its advantages have been described in detail, it should be understood that various changes, substitutions and alterations can be made herein without departing from the spirit and scope of the invention as defined by the appended claims.

What is claimed is:

1. A continuous-range hydrogen sensor comprising:
   a) a resistive surface material;
   b) contact pads of low-resistivity metal serving as electrodes and being in contact with the resistive surface material;
   c) metal nanoparticles arrayed on the resistive surface material with nanobreakjunction gaps between them;
   d) a power supply connected to the contact pads so as to form an electrical circuit of which the resistive surface material is an intergral part; and
   e) a device for measuring changes in one or more electrical properties within the circuit as the nanoparticles are exposed to hydrogen.

2. The continuous-range hydrogen sensor of claim 1, wherein the nanoparticles dissolve hydrogen and have a lattice constant that is sensitive to hydrogen concentration.

3. The continuous-range hydrogen sensor of claim 2, wherein the nanoparticles comprise Pd and Ag.

4. The continuous-range hydrogen sensor of claim 3, wherein the nanoparticles within the array comprise varying amounts of Pd and Ag from particle to particle.

5. A continuous-range hydrogen sensor comprising:
   a) a resistive surface material;
   b) contact pads of low-resistivity metal serving as electrodes and being in contact with the resistive surface material; and
   c) Pd—Ag nanoparticles arrayed on the resistive surface material with nanobreakjunction gaps between them, wherein such nanoparticles expand when exposed to a level of $H_2$ gas suitable for effecting a phase transition of the Pd—Ag alloy, and wherein such expansion fills gaps between the nanoparticles.

6. The continuous-range hydrogen sensor of claim 5, further comprising a power supply connected to the contact pads so as to form an electrical circuit of which the resistive surface material is an intergral part.

7. The continuous-range hydrogen sensor of claim 6, wherein the Pd—Ag nanoparticles within the array comprise varying amounts of Pd and Ag such that nanoparticles of certain Pd:Ag ratios expand when exposed to certain levels of $H_2$ and nanoparticles of other Pd:Ag ratios expand when exposed to other levels of $H_2$, thereby causing electrical shorts that decrease the overall resistance of the sensor in a continuous manner over a range of hydrogen concentrations.

8. The continuous-range hydrogen sensor of claim 7, further comprising a device for measuring changes in the overall resistance of the circuit as a result of changes in the nanoparticles due to their exposure to hydrogen.

9. The continuous-range hydrogen sensor of claim 5, wherein the Ag content ranges from about 0 percent to about 40 percent.

10. The continuous-range hydrogen sensor of claim 5, wherein the nanopoarticles have diameters between about 1 nm and about 100 nm.

11. The continuous-range hydrogen sensor of claim 5, wherein the sensor provides for detection of hydrogen in transformers.

12. The continuous-range hydrogen sensor of claim 5, wherein the sensor provides for detection of hydrogen in applications employing fuel cells.

13. A method comprising the steps of:
   a) forming an array of metal nanoparticles on a resistive surface, wherein nanobreakjunction gaps exist between at least some of the nanoparticles in the absence of hydrogen; and
   b) forming a circuit comprising the resistive surface and a power supply.

14. The method of claim 13, wherein the metal nanoparticles are electrochemically deposited on the resistive surface.

15. The method of claim 14, wherein the nanoparticles undergo a phase change when exposed to certain levels of hydrogen, and wherein such a phase change expands the diameter of the nanoparticles resulting in the closure of at least some nanobreakjunction gaps, thereby producing electrical shorts that increase the flow of current through the circuit.

16. The method of claim 15, wherein the changes in the flow of current through the circuit are correlatable with exposure of the nanoparticles to hydrogen at various concentrations, and wherein such changes provide a means of sensing hydrogen over a continuous range of concentration.

17. The method of claim 14, wherein the nanoparticles undergo phase change gradually.

18. The method of claim 14, wherein the nanoparticles vary in composition and undergo phase changes differentially at differing hydrogen concentrations.

19. The method of claim 15, wherein the nanoparticles comprise Pd and Ag.

20. The method of claim 19, wherein the nanoparticles comprise between about 1 percent and about 40 percent Ag, with the balance being Pd.

* * * * *